United States Patent
Li et al.

(10) Patent No.: US 10,987,416 B2
(45) Date of Patent: Apr. 27, 2021

(54) PURIFICATION OF RECOMBINANT EV71 VIRUS-LIKE PARTICLE AND METHOD FOR PREPARING VACCINE THEREOF

(71) Applicant: BEIJING MINHAI BIOTECHNOLOGY CO., LTD., Beijing (CN)

(72) Inventors: Guoshun Li, Beijing (CN); Meirong Gu, Beijing (CN); Jiankai Liu, Beijing (CN); Lin Guo, Beijing (CN); Lei Chen, Beijing (CN); Gaimei Zhang, Beijing (CN); Yingzhi Xu, Beijing (CN); Jin Li, Beijing (CN); Haifeng Xiao, Beijing (CN)

(73) Assignee: Beijing Minhai Biotechnology Co., Ltd., Beijing (CN)

( * ) Notice: Subject to any disclaimer, the term of this patent is extended or adjusted under 35 U.S.C. 154(b) by 0 days.

(21) Appl. No.: 16/333,290

(22) PCT Filed: Dec. 28, 2016

(86) PCT No.: PCT/CN2016/112636
§ 371 (c)(1),
(2) Date: Mar. 14, 2019

(87) PCT Pub. No.: WO2018/119746
PCT Pub. Date: Jul. 5, 2018

(65) Prior Publication Data
US 2019/0240314 A1    Aug. 8, 2019

(51) Int. Cl.
| | |
|---|---|
| *A61K 39/135* | (2006.01) |
| *C12N 15/81* | (2006.01) |
| *A61P 31/14* | (2006.01) |
| *A61K 39/39* | (2006.01) |
| *A61K 39/12* | (2006.01) |
| *G01N 30/02* | (2006.01) |
| *C12N 7/04* | (2006.01) |
| *A61K 39/125* | (2006.01) |
| *A61K 39/00* | (2006.01) |

(52) U.S. Cl.
CPC ............ *A61K 39/135* (2013.01); *A61K 39/12* (2013.01); *A61K 39/125* (2013.01); *A61K 39/39* (2013.01); *A61P 31/14* (2018.01); *C12N 7/04* (2013.01); *C12N 15/81* (2013.01); *G01N 30/02* (2013.01); *A61K 2039/5258* (2013.01); *A61K 2039/55505* (2013.01); *C12N 2770/32334* (2013.01); *G01N 2030/027* (2013.01)

(58) Field of Classification Search
None
See application file for complete search history.

(56) References Cited

U.S. PATENT DOCUMENTS

2016/0166675 A1    6/2016   Gu et al.

FOREIGN PATENT DOCUMENTS

| CN | 103255163 A | 8/2013 |
|---|---|---|
| CN | 104673760 A | 6/2015 |
| WO | WO14183548 | * 11/2014 |

OTHER PUBLICATIONS

English translation of CN103255163-citation No. 1 in IDS submitted on Mar. 14, 2019.*
English Translation of WO/2014/183548—machine translation, no date.*
International Search Report issued in connection with International Patent Application No. PCT/CN2016/112636.2, 2 pages.

* cited by examiner

*Primary Examiner* — Benjamin P Blumel
(74) *Attorney, Agent, or Firm* — Duane Morris LLP

(57) ABSTRACT

The present invention provides a method for purifying an EV71 virus-like particle and a method for preparing a vaccine thereof. The virus-like particle is obtained by performing high density fermentation cultivation on recombinantly engineered bacteria; inducing expression of the EV71 virus-like particle protein expression using methanol; collecting the bacteria by centrifugation and performing high-pressure homogenization for disruption; performing precipitation on the supernatant with ammonium sulfate; and purifying by redissolution, ultrafiltration, ion exchange chromatography, molecular sieve chromatography, hydroxyapatite chromatography, etc.

8 Claims, 3 Drawing Sheets

PURIFICATION OF RECOMBINANT EV71 VIRUS-LIKE PARTICLE AND METHOD FOR PREPARING VACCINE THEREOF

CROSS REFERENCE TO RELATED APPLICATIONS

This application is a National Stage Application, filed under 35 U.S.C. 371, of International Patent Application No. PCT/CN2016/112636, filed on Dec. 28, 2016, the entirety of which is incorporated by reference herein in its entirety.

TECHNICAL FIELD

The present invention relates to the field of biological products, specifically, to a method for purifying a recombinant EV71 virus-like particle and a method for preparing a vaccine using the purified EV71 virus-like particle.

BACKGROUND ART

Hand-foot-mouth disease (HFMD) is a global infectious disease and is reported in most regions of the world. HFMD is a common pediatric acute infectious disease caused by enterovirus, which can cause the major symptoms of fever, and rash and herpes on mouth, hand, cavity and other parts of the body. Aseptic meningitis, neurogenic pulmonary edema, brainstem encephalitis, myocarditis and the like can occur in a few number of patients. The pathogens of HFMD are mainly enteroviruses, including Coxsackie virus, EV71 and Echovirus, among which EV71 and Cox16 are the most common.

In 1957, it first broke out in New Zealand. In 1969, the EV71 type virus was first confirmed in United States. In the mid-1970s, the epidemic of EV71 with the central nervous system as the main clinical feature sequentially broke out in Bulgaria and Hungary. In Bulgaria alone, 750 cases were reported, 149 people were paralyzed and 44 died. In United Kingdom, the epidemic of HFMD caused by CoxA16 broke out in England and Wales in the fourth quarter of 1994. A total of 952 cases, the largest ever recorded in this country, were observed at the monitoring stations. Most patients were 1-4 years old. In 1997, the epidemic of the HFMD caused by EV71 type occurred in Malaysia, and there were 2,628 cases and 29 deaths from April to August. In 2000, an outbreak of HFMD occurred in Singapore, with 3790 cases and 5 deaths. From September to October in 2000, there were 3790 cases of HFMD, and 5 deaths reported in Singapore, and EV71 was the main pathogen.

In 1981, HFMD was reported in Shanghai, China, and the pathogen was EV71 type virus. In 1983, the epidemic of HFMD occurred in Xiamen, and the CoxA16 virus was isolated from the children patients' specimens. In the same year, HFMD caused by CoxA16 occurred in Tianjin. More than 7,000 cases occurred from May to October, and it broke out again in 1986. In Wuhan in 1995, and in Shenzhen in 1998, EV71 virus was isolated from the children affected with HFMD. HFMD and herpetic angina caused by EV71 occurred in Taiwan in 1998. The number of cases reached 130,000. Nearly 1,700 cases occurred in Zhaoyuan, Shandong province, from May to August in 2000. After 2008, HFMD showed a spreading trend. From March to May in 2008, 3,736 cases, including 22 deaths, were reported in Fuyang, Anhui Province. This disease has been reported in most provinces and regions of China.

At present, the international research on the vaccine against HFMD mainly includes inactivated vaccine, virus-like particle vaccine, subunit vaccine, DNA vaccine and attenuated live vaccine. Despite there are reports on research progress, the subunit vaccine, DNA vaccine, and attenuated live vaccine have not achieved a satisfactory animal protection effect. Certain attenuated live vaccines can also cause mild neurological symptoms, and there are uncertainties in the safety of the vaccine. The research progress of the inactivated vaccine is relatively faster. The EV71 inactivated vaccine developed by Kunming Institute and Beijing Kexing Biological Products Co., Ltd. has been approved for release and selling at the market, but after inactivation of such vaccine, some antigen targets have been destroyed, the immunogenicity is affected thereby, the antigenic purity of the vaccine is low, and the clinical side effects are relatively large. Therefore, the development of a safer and more-effective preventive vaccine against EV71 is of great significance in controlling the epidemic of HFMD in infants and young children.

The emergence of the virus-like particle (VLP) vaccine provides a new opportunity to develop a new safe and effective vaccine. A virus-like particle is a hollow particle containing one or more structural proteins of a certain virus without viral nucleic acid (DNA/RNA), and cannot be autonomously replicated, and it is morphologically identical or similar to a true virus particle, and can be presented to immune cells by the same route as virus infection to effectively induce the body's immune system to produce a protective immune response. The capsid proteins of the virus generally have a natural self-assembly ability. The VLPs vaccine is not infectious, has good stability, is not easy to be inactivated, and has broad development prospects.

The enterovirus belongs to the picornavirus family. The virus particle has an icosahedral symmetrical spherical structure, is stable, not easily mutated, has no envelope and protrusions, and has a diameter of 24 to 30 nm. The nucleic acid is a single plus-strand RNA. The capsid of the virus particle consists of 60 subunits, each of which is assembled from four capsid proteins (VP1-VP4) into a pentameric structure. Studies have shown that the four structural proteins of EV71 virus can be self-assembled into a virus-like particle (VLP) structure in cell, and the VLP structure has a spatial structure similar to that of the natural virus.

At present, the expression systems commonly used for the virus-like particle mainly include prokaryotic expression systems and eukaryotic expression systems. Most of the proteins expressed by the prokaryotic expression systems lose their natural conformation and cannot produce protective antibodies, or the expression products are mostly inclusion bodies, and the denaturation and renaturation for inclusion body involve complicated steps, especially, the expression and purification process of VLP is more complicated. The eukaryotic expression system includes mammalian cell expression system, insect baculovirus expression system, and yeast expression system. In the eukaryotic expression system, proteins can form VLP spontaneously, which provides great convenience for the purification process. However, the use of insect cells to prepare VLP requires relatively high culture conditions and complicated purification process, which limits the requirements of large-scale production. In addition, the baculovirus-insect cell expression system produces baculovirus particles and other contaminants that affect the vaccine effect. The baculovirus particles are difficult to be separated from the prepared VLPs and require inactivation treatment and the like, thus the quality of the vaccine is greatly affected. *Hansenula polymorpha* expression system has the characteristics of stable genetic property, simple operation, high-density fermentation cultivation, high yield of target product, and low production cost, and is suitable for industrialized large-scale production, Hansenula polymorpha expression system also has the advantages of post-translational processing of foreign protein, which processing is not found in the prokaryotic expression system, and is a more advanced VLP vaccine expression system superior to Escherichia coli expression system and other eukaryotic expression systems.

SUMMARY OF THE INVENTION

One purpose of the present invention is to provide a method for purifying an EV71 virus particle expressed from a Hansenula expression system.

Another purpose of the present invention is to provide a recombinant EV71 vaccine.

In order to achieve the above purposes, the present invention provides a method for purifying a recombinant EV71 virus-like particle, comprising the following steps:

(1) performing fermentation on engineered recombinant Hansenula yeast containing a EV71 capsid protein P1 gene and a 3CD protease gene;

(2) disrupting the engineered yeast, and performing precipitation, redissolution and ultrafiltration of the target product;

(3) performing ion exchange chromatography; and (4) performing molecular sieve chromatography or hydroxyapatite chromatography.

For the preparation method of the engineered recombinant Hansenula yeast containing an EV71 capsid protein P1 gene and a 3CD protease gene of the present invention, refer to Chinese Patent ZL201310179673.3.

In the step (1), a formulated high-density culture medium was used for the fermentation of the engineered yeast, glycerin was added intermittently to enable the rapid growth of the, and methanol as an inducer was continuously added to induce the expression of the virus-like particle. At the late stage of fermentation, the engineered yeast were induced under a condition of pH 5.5 for 36 to 42 h.

The disruption of the engineered yeast specifically comprises resuspending the engineered yeast with a cell lysis buffer (20 mM $NaH_2PO_4$, 2 mM $EDTA-Na_2$, 0.2 to 1.0 M NaCl, 2 mM PMSF, 0.1% to 1% Tween-20, pH 6.8 to 7.4), and disrupting the cells for 2 to 4 times using a high-pressure homogenizer at a pressure of 1,100 to 1,400 bar. The cell-disruption rate reaches 80% to 95%.

Preferably, the cells were disrupted for 2 times using a high-pressure homogenizer at a pressure of 1,200 bar.

Precipitation of the target product specifically comprises pouring the cell solution after disruption into a centrifuge bowl, performing centrifugation at 6,000 to 8,000 rpm for 40 to 60 min, collecting the supernatant, adding ammonium sulfate into the collected supernatant to a final concentration of ammonium sulfate of 20 to 28%, and standing overnight. Preferably, the final concentration of ammonium sulfate was 22%.

The redissolution specifically comprises performing centrifugation on the product obtained after precipitation with ammonium sulfate at 8,000 to 10,000 rpm for 40 to 60 minutes, collecting the precipitate, adding a redissolution buffer (20 mM $NaH_2PO_4$, 0.1 to 1.0 M NaCl, pH 6.8 to 7.4), stirring for 30 to 60 min, performing centrifugation at 8,000 to 10,000 rpm for 40 to 60 min, and collecting the redissolution supernatant.

The ultrafiltration specifically comprises subjecting the collected redissolution supernatant to ultrafiltration using a film cassette with a molecular weight cut-off value of 100 to 500 KD, and 20 to 50 mM Tris (pH 7.5 to 8.5) to remove small molecules, and collecting the ultrafiltrate to obtain a crude purified protein solution.

The ion exchange chromatography specifically comprises, taking Capto Q chromatography medium as an example, loading a sample after equilibration with 5 to 10 column volumes of 20 to 50 mM Tris (pH 7.5 to 8.5), eluting with an eluent which contains 20 to 50 mM Tris and 150 to 300 mM NaCl, and collecting the eluate corresponding to a UV absorption peak at 280 nm to obtain a one-step chromatography protein solution. Preferably, the elution was carried out using an eluent of 20 to 50 mM Tris and 230 mM NaCl.

The molecular sieve chromatography specifically comprises, taking Sephacryl S-300HR as an example, purifying the one-step chromatography protein solution with 10 to 50 mM PBS (pH 6.8 to 7.4), 0.1 to 0.3 M NaCl solution and 0.01% to 0.1% Tween-80, and collecting the eluate corresponding to a UV absorption peak at 280 nm to obtain the target protein solution.

The hydroxyapatite chromatography specifically comprises: subjecting the one-step chromatography protein solution to ultrafiltration using a film cassette with a molecular weight cut-off value of 300 KD, and 10 mM PBS (pH 6.8 to 7.4) to remove small molecules, collecting the ultrafiltrate. Loading a sample after equilibration with 5 to 10 column volumes of 10 to 50 mM PBS (pH 6.8 to 7.4), eluting with an eluent of PBS (30 to 200 mM), and collecting the eluate corresponding to a UV absorption peak at 280 nm to obtain the target protein solution.

The present invention also provides a vaccine formulation, wherein each dose of the human vaccine comprises:

2 to 10 μg of recombinant EV71 virus-like particle (based on protein), and 0.10 to 0.30 mg of aluminum adjuvant (based on Al ion).

The present invention provides a method for extracting and purifying a recombinant protein, which has the following advantages:

1. The present invention adopts a formulated high-density culture medium for fermentation of engineered bacteria, and intermittent addition of glycerin and continuous addition of methanol as an inducer, the wet weight of the engineered bacteria after fermentation can reach 300 to 400 g/L, and the expression amount of the antigen can reach $35 \times 10^4$ to $45 \times 10^4$ U/ml.

2. The present invention adopts ammonium sulfate precipitation, PBS redissolution and two-step chromatography, has simple operation and a high recovery rate, and is favorable for large-scale industrialized production.

3. The new vaccine of the present invention is a highly safe recombinant vaccine that does not cause adverse toxic effects and potential risk of RNA carcinogenesis. The vaccine of the present invention uses an aluminum adjuvant, and the immunogenicity of the recombinant EV71 virus-like particle vaccine without aluminum adjuvant is significantly lower than that of the vaccine containing an aluminum adjuvant.

SPECIFIC MODES FOR CARRYING OUT THE EMBODIMENTS

Figure 1:
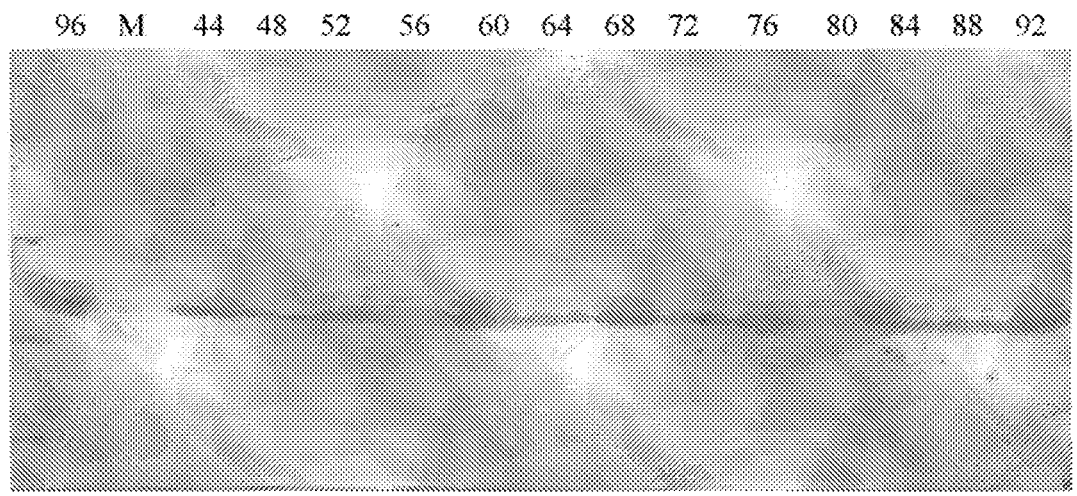
FIG. 1 shows the Western blot detection results of samples of engineered yeast expressing EV71 at different fermentation time (44, 48, 52, 56, 60, 64, 68, 72, 76, 80, 84, 88, 92, and 96 h), and M is a low molecular weight protein standard (Beijing TransGen Company).
Figure 2:
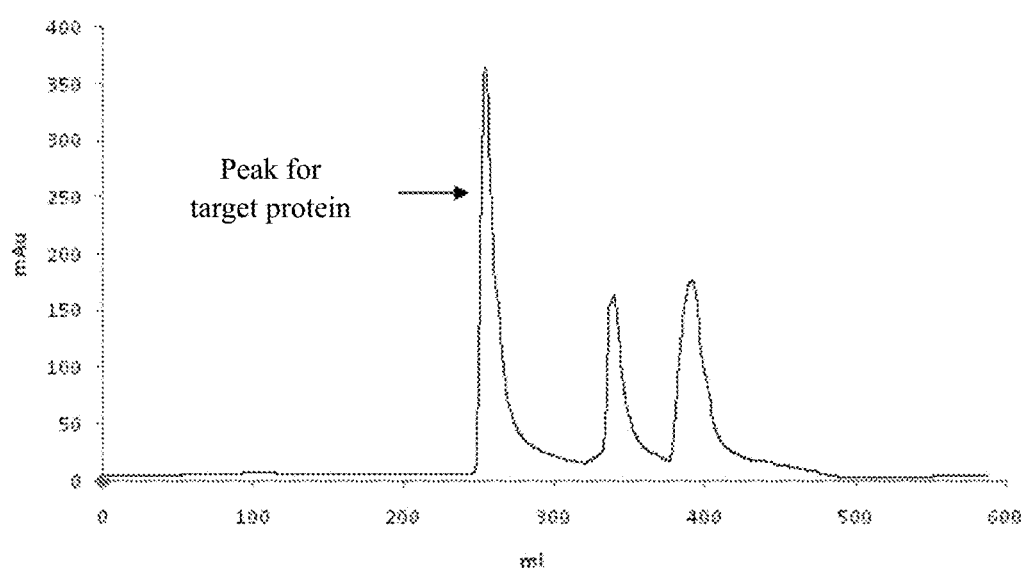
FIG. 2 shows a spectrum for purification by ion exchange chromatography.
Figure 3:
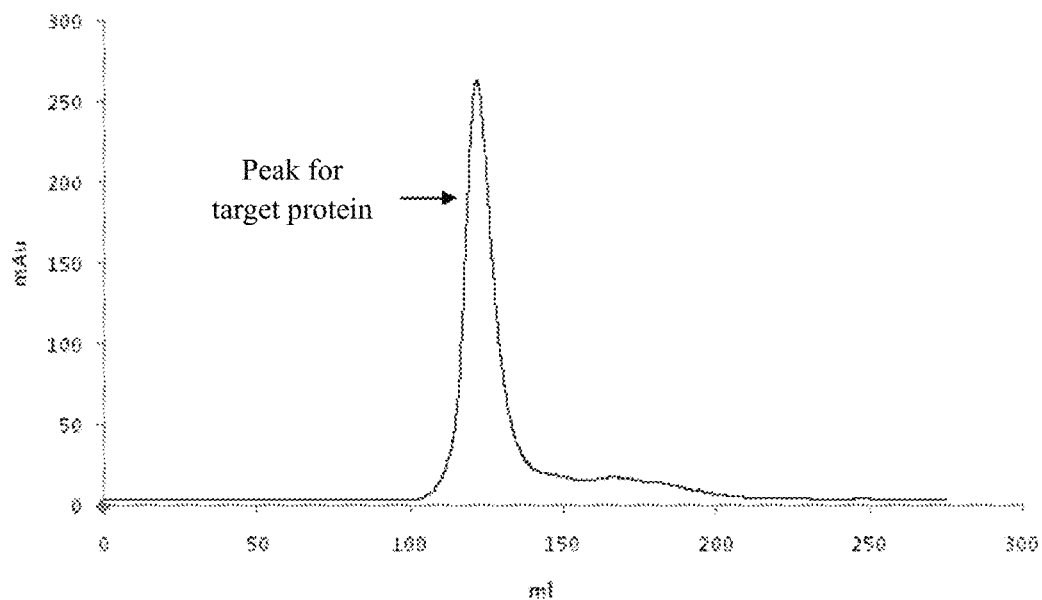
FIG. 3 shows a spectrum for purification by molecular sieve chromatography.

Exemplary embodiments of the present invention are provided in the following Examples. The following Examples are given by way of illustration only and are intended to help a person skilled in the art to use the present invention. The Examples are not intended to limit the scope of the invention in any way.

Example 1: Fermentation Cultivation of a Yeast Strain Expressing Recombinant EV71 Yeast Expressed Strain in a 30 L Fermenter A recombinant *Hansenula* yeast strain (as to the preparation method thereof, see Chinese patent ZL201310179673.3) was inoculated into 150 ml of primary seed culture medium (0.67% nitrogen source medium for yeast, purchased from the SIGMA Inc., 0.5% ammonium sulfate, 2% glucose), followed by shake cultivation at 200 rpm for 20 to 24 h, at 33° C. Then, all of the obtained culture was inoculated into 1,500 ml of secondary seed culture medium (0.67% nitrogen source medium for yeast, 0.5% ammonium sulfate, and 2% glycerin), followed by shake cultivation at 200 rpm for 20 to 24 h ($OD_{600nm}$ reached 8 to 10), at 33° C. Then, all of the obtained culture was inoculated into a 30 L fermenter containing 15 L of fermentation medium (glycerin, ammonium dihydrogen phosphate, potassium chloride, calcium chloride, sodium chloride, magnesium sulfate, and sodium edetate with a mass ratio of 140:70:20:15:18:2:1), the pH value of the fermentation liquid was adjusted with ammonia water to maintain at 5.0, the fermentation temperature was 30° C., the rotation speed was controlled at 350 to 750 rpm, and the air flow rate was 0.5 to 1.0 m³/h. Pure oxygen supplementation was required in high-density fermentation, the dissolved oxygen was controlled at 20% to 60%. The carbon source in the fermentation medium was depleted at 20 to 24 h, a total of 2.0 L of glycerin was supplemented in 5 batches (0.40 L per batch), and glycerin was added when the carbon source was depleted and the dissolved oxygen increased. The bacteria grew for a total of about 36 to 39 hours, and the wet weight of the bacteria reached 0.3 to 0.4 g/ml. The derepression stage: the rotation speed was 750 rpm, the air flow rate was 1.0 m³/h, the dissolved oxygen was controlled at 20% to 60%, and 1 L of a mixed solution of glycerin and methanol (200 ml of glycerin, and 800 ml of methanol) was added to perform derepression cultivation during 36 to 54 h (totally 15 to 18 hours). The induction stage: induction with methanol was performed during 54 to 96 h (36 to 42 hours), and the dissolved oxygen was maintained at about 20% to 40%. The end of the fermentation: at 92 to 96 h, when methanol was completely consumed, the dissolved oxygen increased to 80% or more, and the temperature was decreased to 20° C., the fermentation broth was discharged from the fermenter to finish the fermentation, and the wet weight of the bacterial was maintained at 0.3 to 0.4 g/ml.

Identification of the EV71 virus-like particle expressed by *Hansenula* yeast: samples were taken at different fermentation time described above (at 44, 48, 52, 56, 60, 64, 68, 72, 76, 80, 84, 88, 92 and 96 h) for Western blotting. Anti-EV71-VP1 monoclonal antibody (Jingtiancheng Biotechnology (Beijing) Co., Ltd.) was used as a primary antibody, HRP-goat anti-Mouse-IgG (Beijing Biosynthesis Biotechnology Co., Ltd) was used as a secondary antibody, and DAB was used for color development. The results were shown in FIG. 1.

The results of Western-blot show that the expression product could specifically bond to the monoclonal antibody and has a relatively obvious reaction band at 32.7 KD, indicating that the expression product has good immunoreactivity.

Measurement of expression amount of recombinant EV71 virus-like particle in fermentation: a rabbit polyclonal antibody was 1,000-fold diluted, and a sample of 100 μl was added into the well of a 96-well ELISA plate, followed by coating and standing overnight at 4° C. The coating solution was completely removed, and each well was filled with a PBST wash solution for washing the ELISA plate. The ELISA plate was then filled with a blocking solution (1% BSA in PBST solution), and incubation was performed at 37° C. for 2 h. The supernatant collected by centrifugation after disruption and a national standard for antigen were subjected to gradient serial dilution. After the blocking solution was completely removed, 100 μl of the sample to be tested and 100 μl of the standard were added into each well, and incubation was performed at 37° C. for 1 h. Each well was filled with a PBST wash solution to wash the ELISA plate for 3 times. 100 μl of HRP-labeled mouse monoclonal antibody (1:1,000 diluted) was added into each well, and incubation was performed at 37° C. for 1 h. The solution of HRP-labeled mouse monoclonal antibody was completely removed, and each well was filled with a PBST wash solution to wash the ELISA plate for 3 times. 100 μl of TMB developing solution was added into each well and incubated at 37° C. for 15 minutes in the dark, and 50 μl of 2 mol/L $H_2SO_4$ was added into each well for termination of the reaction. The $OD_{450nm}$ value was measured by a microplate reader, and the antigen content was calculated by a double parallel line method. The detection results were shown in Table 1.

TABLE 1

Detection results of antigen content in fermentation broth after disruption (obtained by ELISA method)

| | Concentration of the national standard for antigen U/ml | | | | |
| --- | --- | --- | --- | --- | --- |
| | Standard 1 80 | Standard 2 40 | Standard 3 20 | Standard 4 10 | Standard 5 5 |
| Average $OD_{450nm}$ value | 2.400 | 1.594 | 0.882 | 0.462 | 0.212 |
| Dilution of sample | 5,000 | 10,000 | 20,000 | 40,000 | 80,000 |

TABLE 1-continued

Detection results of antigen content in fermentation broth after disruption (obtained by ELISA method)

| | Concentration of the national standard for antigen U/ml | | | | |
|---|---|---|---|---|---|
| | Standard 1 80 | Standard 2 40 | Standard 3 20 | Standard 4 10 | Standard 5 5 |
| Average $OD_{45\ nm}$ value of sample | 2.524 | 1.743 | 0.945 | 0.523 | 0.214 |
| Antigen content of fermentation broth after disruption (U/ml) | | | 431,110.4 | | |

The ELISA measurement results show that the antigen content of EV71 virus-like particle in the fermentation broth after cell disruption was $43×10^4$ U/ml. The EV71 expressed by *Hansenula* yeast cells had a relatively high expression quantity.

Example 2: Separation and Purification of EV71 Virus-Like Particle

Cell collection: the fermentation broth was collected and centrifuged at 6,000 rpm, the precipitate was collected and washed twice with a cell washing buffer (20 mmol/L $NaH_2PO_4$, 2 mmol/L EDTA-$Na_2$, 0.4 mol/L NaCl, pH 7.4).

Disruption: the collected *Hansenula* yeast cells were resuspended in a cell lysis buffer (20 mmol/L $NaH_2PO_4$, 2 mmol/L EDTA-$Na_2$, 400 mmol/L NaCl, 2 mmol/L PMSF, 0.1% to 1% Tween-20, pH 7.4), and a high-pressure homogenizer was used to disrupt the cells twice under a pressure of 1,200 bar. The cell disruption rate was 80% or more.

Clarification: the solution after cell disruption was poured into a centrifuge bowl, centrifugation was performed at 6,000 to 8,000 rpm for 40 to 60 min, and the supernatant was collected.

Precipitation of virus-like particle: ammonium sulfate was added into the above collected supernatant to a concentration of ammonium sulfate of about 22% to 28%, followed by standing overnight.

Redissolution: the supernatant of the above solution after precipitation was decanted, and the resultant solution was centrifuged at 10,000 rpm for 40 to 60 min. The precipitate was collected, and a redissolution buffer (20 mmol/L $NaH_2PO_4$, 0.01-1 mol/L NaCl, pH 7.4) was added, followed by stirring for 30 to 60 min, centrifuging at 10,000 rpm for 40 to 60 min, and the redissolution supernatant was collected.

Ultrafiltration: the collected redissolution supernatant was ultrafiltered using a film cassette with a molecular weight cut-off value of 300 KD, and 50 mmol/L Tris (pH 8.0) to remove small molecules, and the ultrafiltrate was collected to obtain a crude purified protein solution.

Ion exchange chromatography: when Capto Q chromatography medium was taken as an example, the sample was loaded after equilibration with 5 to 10 column volumes of 50 mmol/L Tris (pH 8.0), elution was performed using an eluent (50 mmol/L Tris-NaCl (150 to 300 mmol/L)), and the eluate corresponding to a UV absorption peak at 280 nm was collected to obtain a one-step chromatography protein solution. The chromatography medium was regenerated using 1 mol/L NaOH. The purification spectrum was shown in FIG. 2.

Molecular sieve chromatography: Sephaacryl S-300HR was used as a filler, the one-step chromatography protein solution was purified with 10 to 50 mM PB (pH 6.8 to 7.2), 0.1 to 0.3 M NaCl solution and Tween-80 (0.01% to 0.1%), and the eluate corresponding to a UV absorption peak at 280 nm was collected to obtain a target protein solution. The purity of the protein solution detected by HPLC was 100%. The purification spectrum was shown in FIG. 3. The target protein solution obtained by eluting the protein with the eluent containing Tween-80 was more stable, and no precipitation occurred after storage at 4° C. for 12 months.

Hydroxyapatite chromatography: the one-step chromatography protein solution was ultrafiltered using a film cassette with a molecular weight cut-off value of 300 KD, and 10 mmol/L PBS (pH 6.8) to remove small molecules, and the ultrafiltrate was collected. The sample was loaded after equilibration with 5 to 10 column volumes of 10 mmol/L PBS (pH 6.8), elution was performed using an eluent of PBS (30 to 100 mmol/L), and the eluate corresponding to a UV absorption peak at 280 nm was collected to obtain a target protein solution.

Detection of target protein concentration (Lowry method): 0 ml, 0.2 ml, 0.4 ml, 0.6 ml, 0.8 ml, and 1.0 ml of standard protein bovine serum albumin solution (200 μg/ml) were accurately added into a test tube, respectively. Distilled water was added to make up to 1 ml, meanwhile, 1 ml of a purified protein solution (5-fold diluted) was added into a test tube. The obtained standard protein solution and the purified protein solution are, respectively, added with 5 ml of alkaline copper solution and 0.5 ml of phenol reagent and measured in a cuvette for the absorbance value at a wavelength of 650 nm. A standard curve was plotted with the protein content of the standard protein as the abscissa and the absorbance value as the ordinate, and the concentration of the protein to be detected was calculated. The detection results were shown in Table 2.

TABLE 2

| Detection results of the concentration of purified protein (Lowry method) | | | | | | |
|---|---|---|---|---|---|---|
| | Standard 1 | Standard 2 | Standard 3 | Standard 4 | Standard 5 | Standard 6 |
| Concentration of standard μg/ml | 0 | 40 | 80 | 120 | 160 | 200 |
| OD650 nm | 0.000 | 0.138 | 0.256 | 0.366 | 0.452 | 0.586 |
| OD650 nm of | 0.255 | 0.249 | Average OD650 nm value | | | 0.307 |

TABLE 2-continued

Detection results of the concentration of purified protein (Lowry method)

|  | Standard 1 | Standard 2 | Standard 3 | Standard 4 | Standard 5 | Standard 6 |
|---|---|---|---|---|---|---|
| sample Calculated concentration μg/ml |  | 118.5 | Dilution multiple | 8 | Final concentration of purified protein solution μg/ml | 948 |

The detection result (Lowry method): the final concentration of the purified protein was 948 μg/ml.

Figure 4:
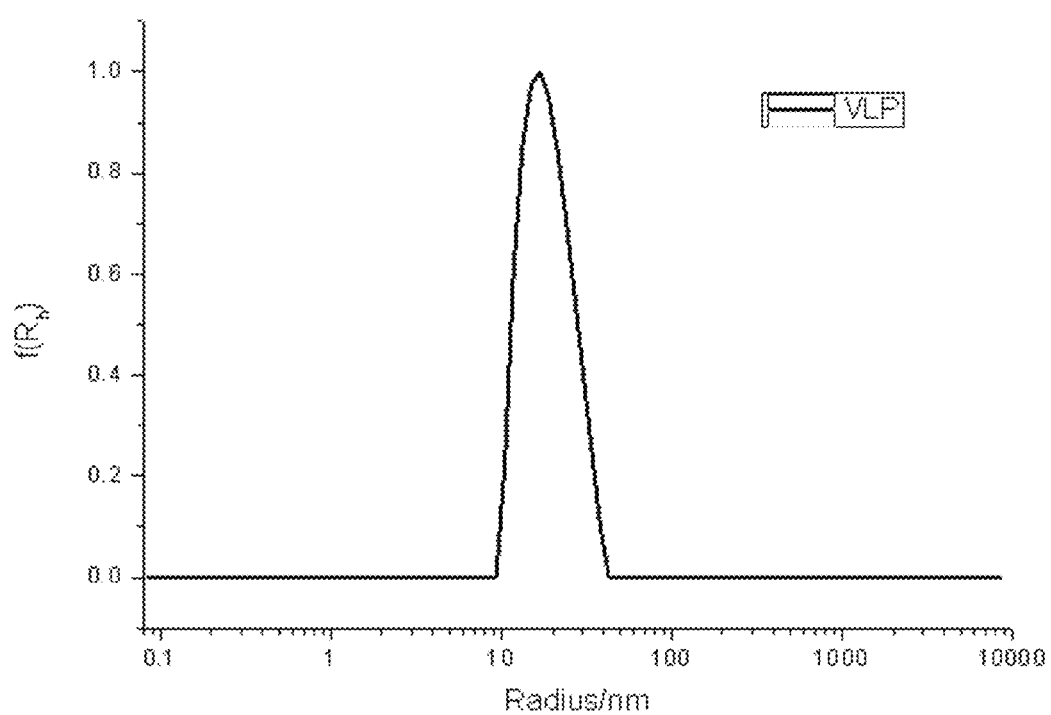
FIG. 4 shows a dynamic light scattering spectrum of the purified EV71 virus-like particle.

Dynamic light scattering analysis of the target protein solution: a proper amount of the purified EV71 protein solution was added into a sample cell, the temperature was set at 25° C., the equilibrium time was set to be 90 s, the number of cycle was set automatically, then the measurement was started, and the results were analyzed. The results show that the recombinant EV71 virus-like particles were intact, and 99% or more of them had a diameter of 24 to 30 nm. The dynamic light scattering spectrum was shown in FIG. 4.

Figure 5:
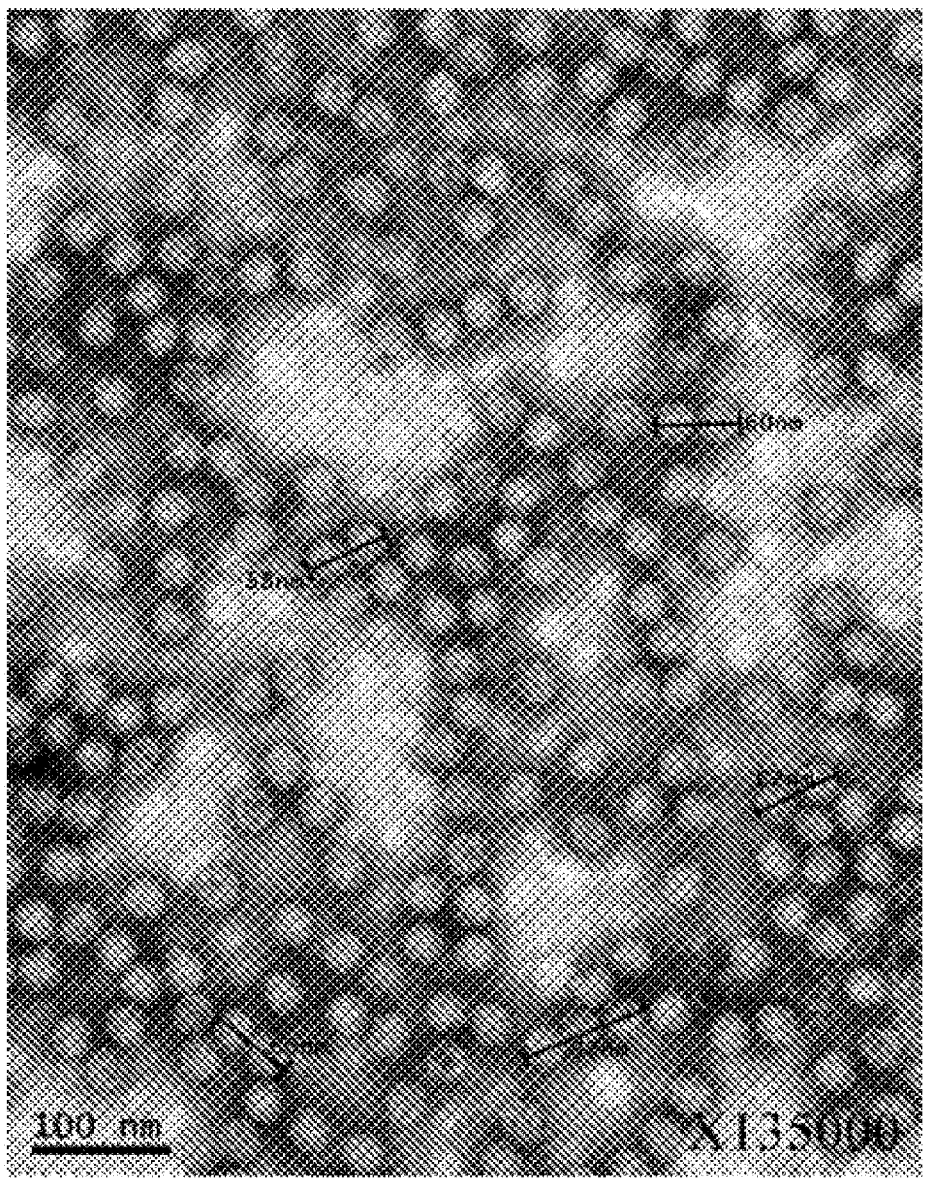
FIG. 5 shows a transmission electron microscopy image of the purified EV71 virus-like particle (magnification time: 135,000).

Electron microscope analysis of the target protein solution: a proper amount of the purified EV71 protein solution was added dropwise onto a copper mesh and stored for 5 min in the dark. The excessive solution was removed, and 1% phosphotungstic acid was used for staining for 2 min. The EV71 VLPs were analyzed using a transmission electron microscope (TEM). The results show that the EV71 protein was present as a virus-like particle which had a regular icosahedral structure of natural viruses. The diameter of the virus particle was about 30 nm, and the particle was intact and regular (as shown in FIG. 5, magnification times: 135,000).

Determination of antigen content of the target protein solution (double-antibody sandwich ELISA): a rabbit polyclonal antibody was 5,000-fold diluted and 100 μl of the resultant was added into the well of a 96-well ELISA plate, followed by coating and standing overnight at 4° C. The coating solution was completely removed, and each well was filled with a PBST wash solution to wash the ELISA plate. The ELISA plate was filled with a blocking solution (1% BSA in PBST solution), and incubation was performed at 37° C. for 2 h. The blocking solution was completely removed, 100 μl of the sample to be detected was added into each well, and incubation was performed at 37° C. for 1 h. Each well was filled with a PBST wash solution, and the ELISA plate was washed for 3 times. 100 μl of HRP-labeled mouse monoclonal antibody (1:1,000 diluted) was added into each well, and incubation was performed at 37° C. for 1 h. The solution of HRP-labeled mouse monoclonal antibody was completely removed, each well was filled with a PBST wash solution, and the ELISA plate was washed for 3 times. 100 μl of TMB developing solution was added into each well at 37° C. for 15 minutes in the dark, and 50 μl of 2 mol/L $H_2SO_4$ was added into each well for termination of the reaction. The $OD_{450nm}$ value was measured by a microplate reader, and the antigen content was calculated by a double parallel line method. The detection results of the double-antibody sandwich ELISA were shown in Table 3.

TABLE 3

Detection results of the double-antibody sandwich ELISA

| | Concentration of the standard U/ml | | | | |
|---|---|---|---|---|---|
| | Standard 1 80 | Standard 2 40 | Standard 3 20 | Standard 4 10 | Standard 5 5 |
| Average OD450 nm value | 2.917 | 2.452 | 1.492 | 0.849 | 0.458 |
| Dilution of sample | 10,000 | 20,000 | 40,000 | 80,000 | 160,000 |
| Average OD450 nm value of sample | 2.535 | 1.627 | 1.031 | 0.549 | 0.299 |
| Antigen content of the purified protein solution (U/ml) | | | 468980 | | |

Example 3: Preparation of Recombinant EV71 Virus-Like Particle Vaccine

Control of main indicator: The antigen (EV71 virus-like particle) content was 10 μg/ml; the aluminum content was controlled at 0.40 to 0.60 mg/ml; and the pH value was controlled at 6.6 to 7.0.

Preparation method: A sterile PBS solution was injected into a tank. Mechanical stirring at a rotation speed of 500 to 700 rpm was used, and air was introduced into the tank to maintain a pressure of 0.05 to 0.1 MPa. A filtration-sterilized aluminum potassium sulfate solution was slowly added into the tank, and then a sodium hydroxide solution was added dropwise until the pH was 6.6 to 7.0. After standing, a sterile 0.9% sodium chloride solution was used to replace the supernatant for 4 to 5 times, and the preparation of an aluminum hydroxide adjuvant was completed. The stock solution of the purified EV71 was slowly added dropwise into the adjuvant, so that the protein could be fully adsorbed, and the preparation of the vaccine was completed. The detection standards and detection results of the prepared vaccine were shown in Table 4.

TABLE 4

Detection results of the recombinant EV71 virus-like particle vaccine

| Detection item | Quality standard | Detection result |
|---|---|---|
| Relative effectiveness | Not less than 2.0 | 3.1 |
| Aluminum content | 0.40 to 0.60 mg/ml | 0.50 mg/ml |
| pH value | 6.0 to 8.0 | 6.9 |

TABLE 4-continued

Detection results of the recombinant EV71 virus-like particle vaccine

| Detection item | Quality standard | Detection result |
| --- | --- | --- |
| Adsorption rate | >95% | 99.2% |
| Osmolality | 300 ± 65 mOSmol/kg | 292 mOSmol/kg |
| Bacterial endotoxin | Less than 5 EU/ml | Meet the requirements |

The results in Table 4 show that all the detection indicators of the recombinant EV71 virus-like particle vaccine meet the detection standards.

Example 4: Immunogenicity ($ED_{50}$) Assay of the Recombinant EV71 Virus-Like Particle Vaccine Experimental vaccine: The recombinant EV71 virus-like particle vaccine containing an aluminum hydroxide adjuvant prepared in Example 3.

Experimental animals: 50 BALB/c mice of SPF grade (18 to 22 g) were selected and the mice were purchased from Beijing Vital River Laboratory Animal Technology Co., Ltd.

Animal immunization: 0.5, 0.125, 0.03125, and 0.0078125 μg/0.5 ml of proportionally diluted vaccines and the aluminum hydroxide adjuvant were injected into 10 mice (intraperitoneal injection of 0.5 ml for each mouse), respectively, and the eyeballs were taken for collecting blood at 28 days after immunization. The collected blood was stored at 37° C. for 1 h, followed by standing at 4° C. for 3 to 4 h, centrifuging at 4,000 rpm for 10 min, and the supernatant was collected for detection.

Neutralizing antibody detection: serum samples were diluted at a proportion of 1:8 with MEM medium of 2% newborn bovine serum, and inactivation was performed in a water bath at 56° C. for 30 min. A 96-well cell culture plate was used, and 50 μl of diluent was added into each well. 50 μl of the corresponding sample was added into each well, after the solution in wells of row A were mixed well, a multichannel pipette was used to aspirate 50 μl solution from row A, add the solution into wells in row B and mix the resultant solution well, then sequential dilution and mixing from row B to row D were performed, and 50 μl solution was discarded. The EV71 virus for virus challenge was serially diluted to 100 $CCID_{50}$/0.05 ml, 50 μl of the diluted solution was vertically dripped into each well, and the mixture in the well was mixed well by gently tapping the cell culture plate, and neutralized at 37° C. for two hours. A cell dissociation solution was used for dissociating RD cells (the cells were resuscitated and proliferated in advance), a cell suspension with a concentration of $2\times10^5$ cells/ml was prepared, 0.1 ml of the cell suspension was added into each well (including virus back titration wells), mixed well, and placed into a $CO_2$ incubator for incubation at 35° C. CPE was observed daily using an inverted microscope, results of virus titration were recorded, and the reciprocal of the highest dilution of serum capable of inhibiting 50% of the cytopathic effect was taken as the endpoint titer. The final result was judged in 6 to 7 days. According to the detection results, the antibody positive conversion rate was shown in Table 5.

TABLE 5

Results of Calculating antibody positive conversion rate

| | | Mouse antibody | | Positive conversion rate | Total | | Positive conversion rate |
| --- | --- | --- | --- | --- | --- | --- | --- |
| Dilution | Protein content | Positive | Negative | | Positive | Negative | |
| 1:10 | 0.5 μg/0.5 ml | 10 | 0 | 100% | 32 | 0 | 100.00% |
| 1:40 | 0.125 μg/0.5 ml | 10 | 0 | 70% | 22 | 0 | 100.00% |
| 1:160 | 0.03125 μg/0.5 ml | 7 | 3 | 70% | 12 | 3 | 80.00% |
| 1:640 | 0.0078125 μg/0.5 ml | 5 | 5 | 50% | 5 | 8 | 38.46% |

$ED_{50}$=0.011 (μg), calculated according to the Reed-Muench method:

It can be seen from the results of the $ED_{50}$ assay of the mouse that the EV71 virus-like particle vaccine prepared by the present invention could achieve an antibody positive conversion rate of 50% after the mouse is immunized with only 0.011 μg, therefore the EV71 virus-like particle of the present invention has strong immunogenicity.

Example 5: Abnormal Toxicity Assay of the Recombinant EV71 Virus-Like Particle Vaccine Vaccine sample: the recombinant EV71 virus-like particle vaccine prepared in Example 3.

Experimental animals: five KM mice of SPF grade (18 to 22 g) and two Hartley guinea pigs of SPF grade (250 to 350 g), both purchased from Beijing Vital River Laboratory Animal Technology Co., Ltd.

Experimental method: the body weight of each experimental animal was weighed before injection, the mouse was 18 to 22 g, and the guinea pig was 250 to 350 g. The vaccine was injected into five mice and two guinea pigs. The mice were intraperitoneally injected with 0.5 ml per mouse, and the guinea pigs were intraperitoneally injected with 5.0 ml per guinea pig, followed by observation for 7 days. At the same time, the same batch of animals was served as the blank control group. Qualified standard: during the observation period, the animals of the blank control group and experimental group were alive and healthy, with no abnormal actions, and the weight of each animal increased. Results of the animal experiment were shown in Table 6.

TABLE 6

Results of animal experiment

| Animal type | No. | Initial Weight (g) | Final Weight (g) |
| --- | --- | --- | --- |
| Mouse experimental group | 1 | 20.7 | 32.2 |
| | 2 | 21.9 | 35.3 |
| | 3 | 21.5 | 35.3 |

TABLE 6-continued

Results of animal experiment

| Animal type | No. | Initial Weight (g) | Final Weight (g) |
|---|---|---|---|
| | 4 | 19.8 | 35.4 |
| | 5 | 20.8 | 30.8 |
| Guinea pig experimental group | 1 | 325.0 | 413.0 |
| | 2 | 320.5 | 392.0 |
| Mouse control group | 1 | 20.4 | 32.1 |
| | 2 | 20.8 | 32.0 |
| | 3 | 21.2 | 32.6 |
| | 4 | 19.8 | 34.7 |
| | 5 | 20.6 | 37.7 |
| Guinea pig control group | 1 | 314.2 | 376.3 |
| | 2 | 323.7 | 387.4 |

Conclusion: during the observation period, the animals of the blank control group and experimental group were alive and healthy, with no abnormal actions. On the 8th day, the weight of each animal increased. It was proved that the recombinant EV71 virus-like particle vaccine had no abnormal toxicity, and has good safety for experimental animals.

INDUSTRIAL APPLICABILITY

The present invention provides a method for purifying an EV71 virus-like particle and a method for preparing a vaccine using the purified EV71 virus-like particle. The virus-like particle is obtained by performing high density fermentation cultivation on recombinantly engineered yeast; inducing EV71 virus-like particle protein expression using methanol; collecting the yeast by centrifugation and performing high-pressure homogenization for disruption; performing precipitation on the supernatant with ammonium sulfate; and purifying the particle by redissolution, ion exchange chromatography, molecular sieve chromatography, hydroxyapatite chromatography, etc. The EV71 virus-like particle vaccine provided by the present invention has good immunogenicity, safety, immunological characteristics and biological activity, has a simple process, does not use large equipment of ultracentrifuge, is more easily prepared and purified on a large scale, can be used for preparing a vaccine for preventing EV71 infection, and has good economic value and application prospects.

What is claimed is:

1. A method for purifying a recombinant EV71 virus-like particle, comprising steps of:
   (1) performing fermentation on engineered recombinant *Hansenula* yeast containing a EV71 capsid protein P1 gene and a 3CD protease gene;
   (2) disrupting the engineered yeast, and performing precipitation, redissolution and ultrafiltration of the recombinant EV71 virus-like particle;
   (3) performing ion exchange chromatography; and
   (4) performing molecular sieve chromatography or hydroxyapatite chromatography, wherein the step of precipitating the recombinant EV71 virus-like particle in the step (2) comprises pouring cell solution after disruption into a centrifuge bowl, performing centrifugation at 6,000 to 8,000 rpm for 40 to 60 min, collecting a supernatant, and adding ammonium sulfate into the collected supernatant to a final concentration of 20 to 28%.

2. The method according to claim 1, wherein the step for disrupting the engineered yeast in the step (2) comprises resuspending the engineered yeast with a cell lysis buffer, and disrupting cells for 2 to 4 times by a high-pressure homogenizer at a pressure of 1,100 to 1,400 bar; and the cell lysis buffer comprises 20 mM $NaH_2PO_4$, 2 mM EDTA-$Na_{2,\,0.2}$ to 1.0 M NaCl, 2 mM PMSF, 0.1% to 1% Tween-80 and has a pH of 6.8 to 7.4.

3. The method according to claim 1, wherein the redissolution in the step (2) comprises performing centrifugation on the product obtained by precipitation with ammonium sulfate at 8,000 to 10,000 rpm for 40 to 60 min, collecting the precipitate, adding a redissolution buffer, stirring for 30 to 60 min, performing centrifugation at 8,000 to 10,000 rpm for 45 to 60 min, and collecting the supernatant, wherein the redissolution buffer comprises 20 to 50 mM $NaH_2PO_4$, 0.1 to 1 M NaCl and has a pH of 6.8 to 7.4.

4. The method according to claim 1, wherein the ultrafiltration in the step (2) comprises subjecting the supernatant collected after redissolution to ultrafiltration using a film cassette with a molecular weight cut-off value of 100 to 500 KD, and 20 to 50 mM Tris at pH 7.5 to 8.5 to remove small molecules, and collecting the ultrafiltrate to obtain a crude purified protein solution.

5. The method according to claim 1, wherein the ion exchange chromatography in the step (3) comprises loading a sample after equilibration with 5 to 10 column volumes of 20 to 50 mM Tris at pH 7.5 to 8.5, eluting with an eluent of 20 to 50 mM Tris and 150 to 300 mM NaCl, and collecting the eluate corresponding to a UV absorption peak at 280 nm to obtain a one-step chromatography protein solution.

6. The method according to claim 5, wherein the molecular sieve chromatography method in the step (4) comprises purifying the one-step chromatography protein solution obtained in the step (3) with 10 to 50 mM PB at pH of 6.8 to 7.2, 0.1 to 0.3 M NaCl solution and 0.01% to 0.1% Tween-80, and collecting the eluate corresponding to a UV absorption peak at 280 nm to obtain a target protein solution.

7. The method according to claim 5, wherein the hydroxyapatite chromatography method in the step (4) comprises subjecting the one-step chromatography protein solution obtained in the step (3) to ultrafiltration using a film cassette with a molecular weight cut-off value of 100 to 500 KD with 10 to 50 mM PBS at pH 6.8 to 7.4 to remove small molecules, collecting the ultrafiltrate; loading a sample after equilibration with 5 to 10 column volumes of 10 to 50 mM PBS at pH 6.8 to 7.4, eluting with 30 to 200 mM PBS to obtain a target protein solution.

8. A method for preparing of a vaccine against hand-foot-mouth disease, comprising purifying a recombinant EV71 virus-like particle according to the method of claim 1.

\* \* \* \* \*